United States Patent [19]

Armstrong et al.

[11] Patent Number: 4,553,932
[45] Date of Patent: Nov. 19, 1985

[54] METHOD AND IMPLEMENT FOR PULLING BONDED ORTHODONTIC BRACKETS OFF TEETH

[75] Inventors: Maclay M. Armstrong, 17001 - 14th NW., Seattle, Wash. 98177; John R. Rogers, Bellevue, Wash.; Steven A. Houser, Everett, Wash.

[73] Assignee: Maclay M. Armstrong, Seattle, Wash.

[21] Appl. No.: 490,092

[22] Filed: Apr. 29, 1983

[51] Int. Cl.⁴ .............................................. A61C 7/00
[52] U.S. Cl. ...................................................... 433/4
[58] Field of Search ................................ 433/3, 4, 159

[56] References Cited

U.S. PATENT DOCUMENTS

| | | | |
|---|---|---|---|
| 442,107 | 12/1890 | Davison | 433/159 |
| 3,507,043 | 4/1970 | Rubin | 433/4 |
| 3,755,902 | 9/1973 | Northcutt | 32/66 |
| 3,986,265 | 10/1976 | Cusato | 32/66 |
| 4,248,587 | 2/1981 | Kurz | 433/4 |

Primary Examiner—Robert Peshock
Attorney, Agent, or Firm—Robert W. Beach; Ward Brown

[57] ABSTRACT

A pistol grip has twin abutments projecting in parallel relationship and spaced apart to straddle an orthodontic bracket attached to a tooth and to engage the tooth at opposite sides of the bracket. A swing handle pivoted to the pistol grip carries a pull wire extending between the abutments such pull wire has a loop for hooking a wing of the orthodontic bracket. The handle can be pulled toward the pistol grip to draw the pull wire toward the pistol grip for pressing the abutments against the tooth and simultaneously pulling the bracket off the tooth. During such pulling, constriction of the arch wire slot in the bracket is prevented by fitting in such slot a spacer hook of a tenaculum.

21 Claims, 12 Drawing Figures

U.S. Patent  Nov. 19, 1985  Sheet 1 of 3  4,553,932
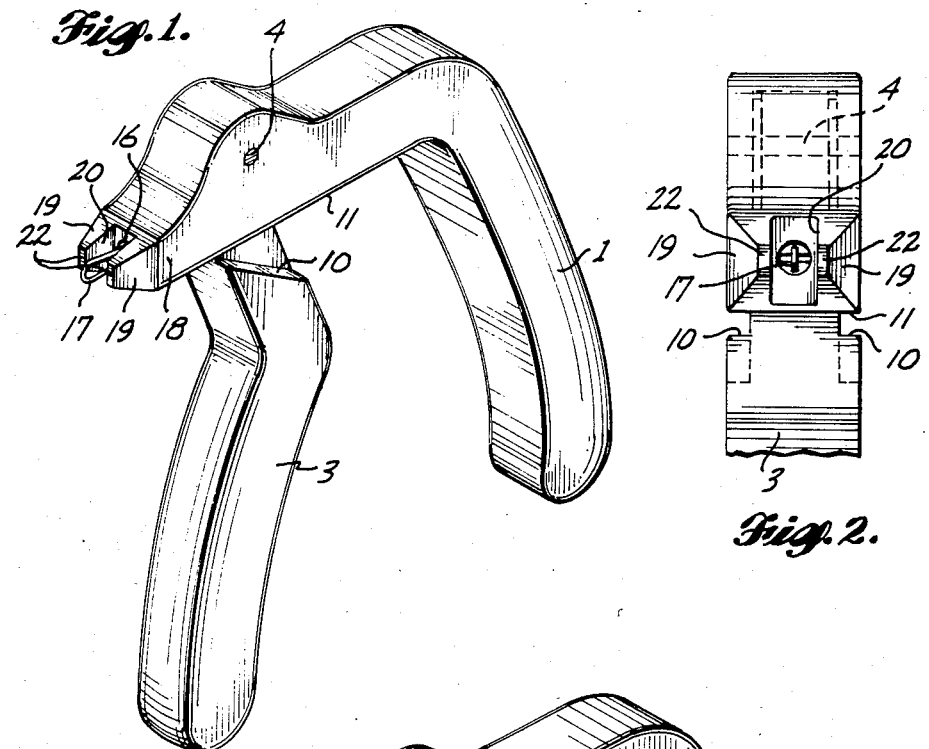
Fig. 1.
Fig. 2.
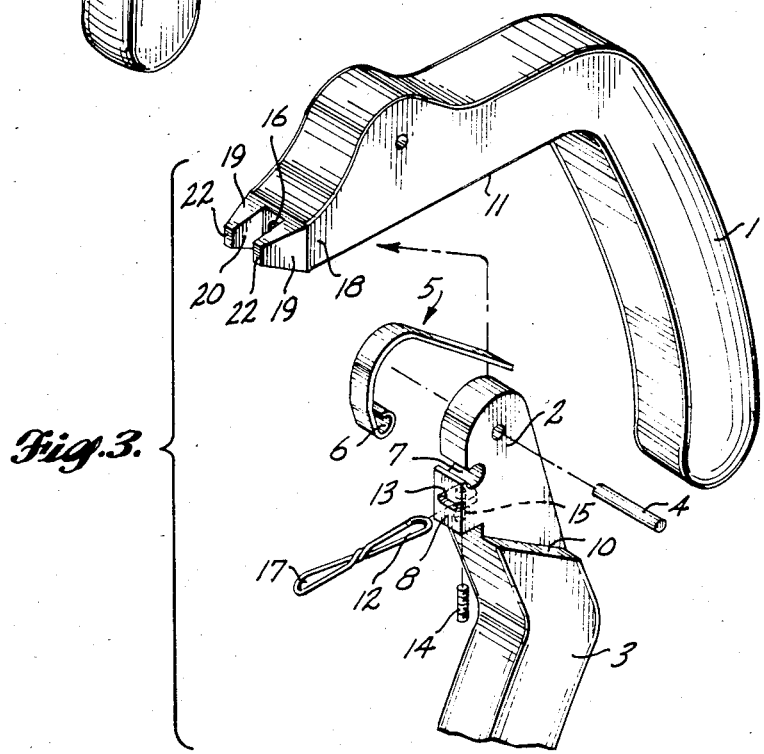
Fig. 3.

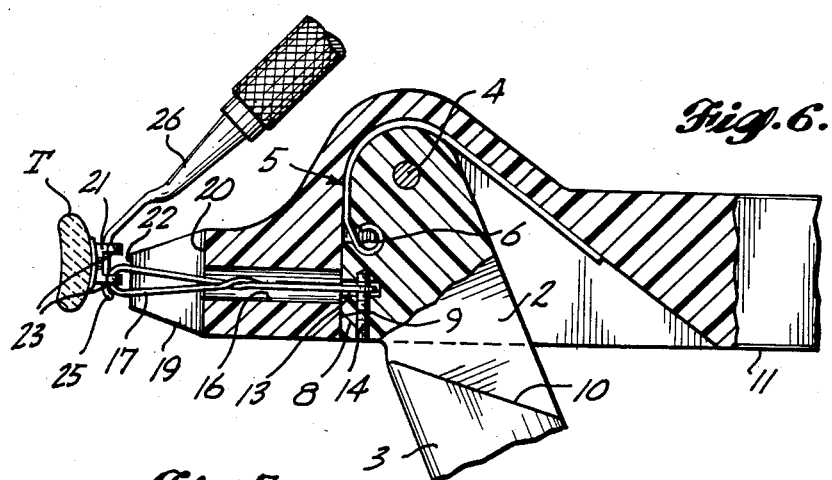
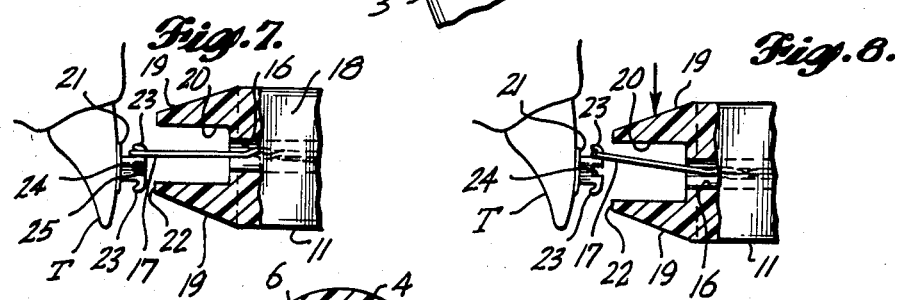
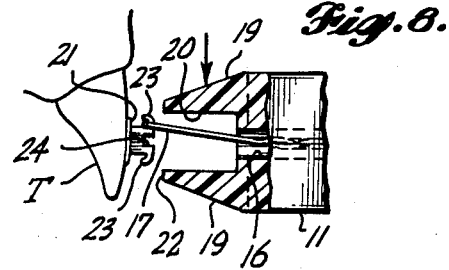
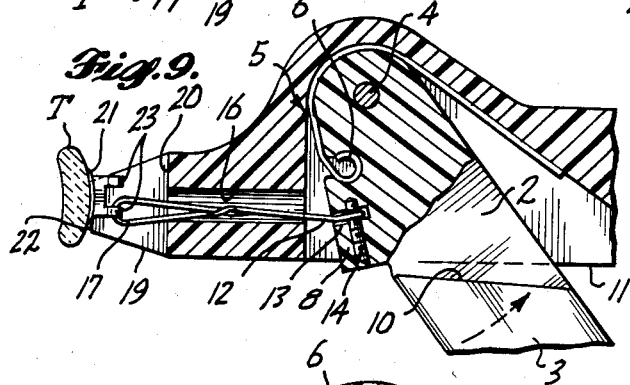
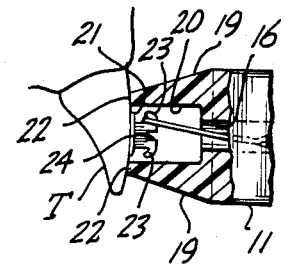
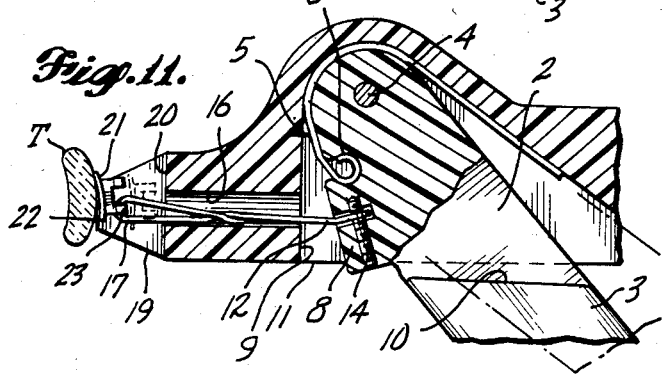
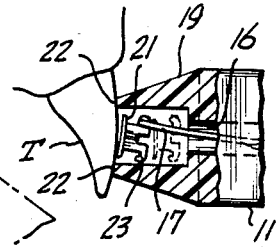

METHOD AND IMPLEMENT FOR PULLING BONDED ORTHODONTIC BRACKETS OFF TEETH

BACKGROUND OF THE INVENTION

1. Field of the Invention

This invention relates to a method and implement for pulling off teeth orthodontic brackets bonded to them and, in particular, differs from removing such orthodontic brackets by manipulations other than pulling such brackets off teeth.

2. Prior Art

Prior practices for removing from teeth orthodontic brackets bonded to them have utilized prying action.

The Northcutt U.S. Pat. No. 3,755,902, issued Sept. 4, 1973, states at column 1, lines 9 to 11 that at the time of that patent there was no known tool which could accomplish the removal of onlays or brackets from teeth to which they had been cemented. The pliers disclosed in that patent included an edge 35 that pried the onlay or bracket from the tooth surface.

Three years later the Cusato U.S. Pat. No. 3,986,265, issued Oct. 19, 1976, disclosed a plier type orthodontic tool for removing orthodontic brackets by a prying action, as stated at column 1, lines 27 and 41 and column 4, lines 31 and 34.

The recent Kurz U.S. Pat. No. 4,248,587, issued Feb. 3, 1981, discloses specially constructed plyers, as stated in the Abstract, which remove brackets and tubes bonded to the surfaces of teeth by catches that extend under the edge of the bracket, as stated at column 2, lines 7 to 10 and 34 to 37.

SUMMARY OF THE INVENTION

It is a principal object of the present invention to provide an implement for removing orthodontic brackets bonded to teeth which is easy and quick to use and the operation of which is reliable.

A further object is to provide an implement for removing bonded brackets by the application of a small force and which implement has no appreciable tendency to slip inadvertently during use.

Another object is to provide a method and implement for removing orthodontic brackets bonded to teeth which will not apply appreciable force to the periodontal membrane and, consequently, will avoid causing the patient pain or trauma.

It is also an object to provide a method and implement for removing bonded orthodontic brackets which will not cause any damage to the teeth.

An additional object is to provide an instrument which is inexpensive to make and is durable.

It is a further object to control the bracket when it is released from the tooth so that it can be recovered easily.

Still another object is to utilize a method and implement for removing bonded orthodontic brackets which will avoid distortion of the brackets so that they can be reused.

The foregoing objects can be accomplished by an orthodontic bracket puller than can pull a bracket from a tooth in a controlled manner, by exerting a pull on a bracket wing which will tilt the bracket relative to the tooth at the same time that a reaction force is applied to the same tooth to counteract the pulling force.

BRIEF DESCRIPTION OF THE DRAWINGS

FIG. 1 is a top perspective of an orthodontic bracket puller according to the present invention.

FIG. 2 is a fragmentary elevation of the head of the puller.

FIG. 3 is a top perspective of the orthodontic bracket puller similar to FIG. 1 but showing parts in exploded relationship.

FIG. 6 is a plan of the head portion of the puller with parts broken away.

FIG. 7 is a fragmentary side elevation of the nose portion of the puller with parts broken away, and FIG. 8 is a similar view with parts shown in somewhat different positions.

FIG. 9 is a plan of the head portion of the puller corresponding to FIG. 6 but with parts in different operative relationships.

FIG. 10 is a fragmentary elevation of the nose portion of the puller with parts broken away and with parts shown in the relationship of FIG. 9.

FIG. 11 is a plan of the head portion of the puller with parts broken away corresponding to FIGS. 6 and 9 but with parts shown in different positions.

FIG. 12 is a fragmentary elevation of the nose portion of the puller with parts broken away corresponding to FIGS. 7, 8 and 10, but having parts in the different positions of FIG. 11.

DETAILED DESCRIPTION

Figure 5:
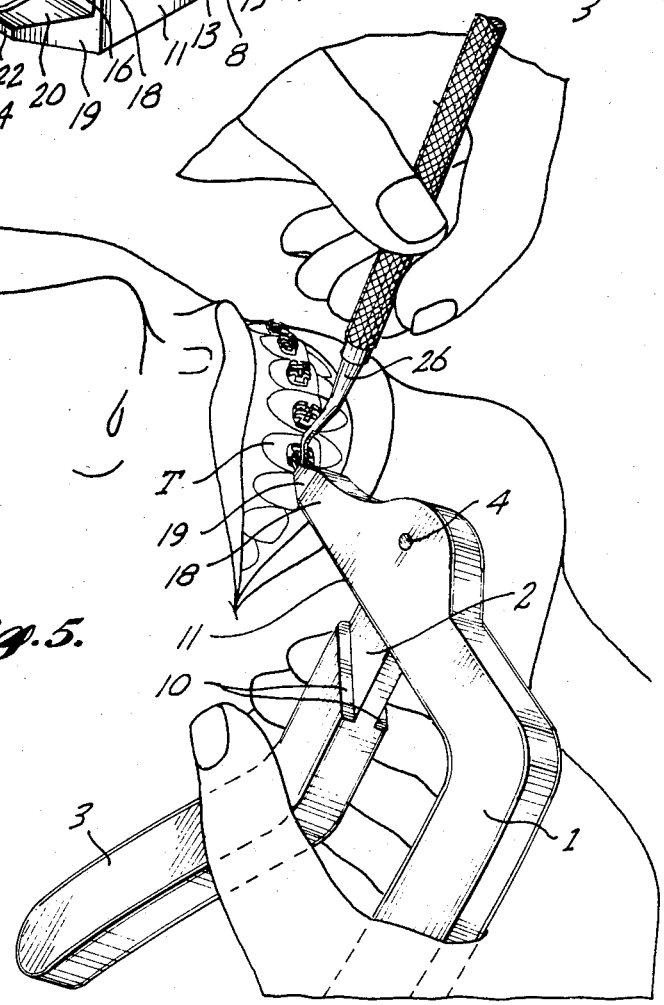
FIG. 5 is a top perspective illustrating a bracket-pulling operation using the puller and a tenaculum.

The pulling implement body 1 of the present invention is of the gun type including a pistol grip extending transversely from a head portion. Such head portion has a cavity for receiving an end portion 2 of a swing handle 3 projecting from the body head portion generally parallel to the pistol grip as shown in FIGS. 1 and 5. Such end portion of the swing handle is secured in the head portion cavity by a fulcrum pivot pin 4. The swing handle is urged to swing away from the pistol grip by a body head portion 5 received in the pistol grip cavity and having a curled end 6 fitting in a cylindrical groove 7 in the end portion 2 of the swing handle inserted into the body head portion cavity. The major portion of such spring is curved generally concentrically with the swing handle pivot 4 but is flatter adjacent to its free end remote from its curled end 6. The free end of the strip spring bears against the inner wall of the body head portion cavity so that the tendency of the spring to straighten provides a force urging the swing handle to swing in a direction to press end 2 to swing its insert end 2 to swing its edge 8 of its end portion inserted into the body head portion cavity against the forward wall 9 of the such cavity in the position shown in FIG. 6. Retracting movement of the swing handle toward the pistol grip in opposition to the force of spring 5 is limited by engagement of the shoulders 10 of the swing handle at the root of its end portion 2 inserted into the body head portion cavity with the edges 11 of the such cavity.

Figure 4:
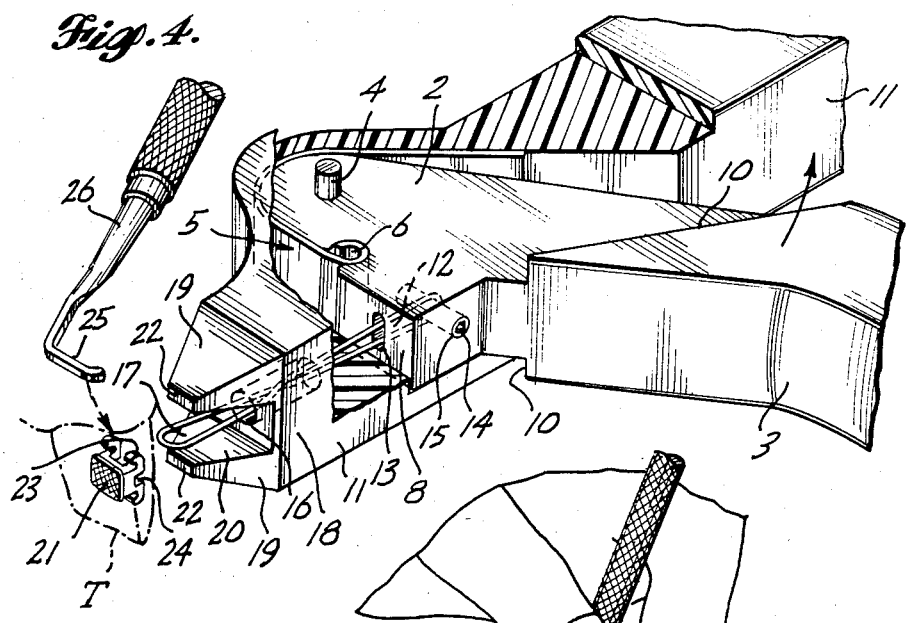
FIG. 4 is an enlarged fragmentary top perspective of the orthodontic bracket puller head portion with parts broken away.

A double loop pull wire has a loop 12 that can be secured in a socket 13 in the edge 8 of the swing handle end portion 2 at a location spaced from the fulcrum pivot 4 to provide lever means with the swing handle of the second-class type, i.e. lever means in which the load, represented by the wire loop 12, and the power applicator, represented by the grip of the swing handle 2, are at the same side of the fulcrum pivot 4, the load is between the pivot fulcrum and the power applicator, the movement of the power applicator is greater than the movement of the load and the force of the power applicator is correspondingly less than the force of the load. The pull wire loop is anchored in such socket by a screw 14 screwed into a tapped bore 15 having portions at opposite sides of the socket. As shown in FIG. 4, such pull wire socket 13 is located in the lever arm at the same side of the fulcrum pivot 4 as the handle 3 and the distance between such pull wire socket and the fulcrum pivot 4 is a small fraction of the length of the lever arm, such as approximately one-eighth, as shown in FIG. 1. Such screw will extend through the loop 12 when the loop is inserted sufficiently far into the socket. The pull wire extends through a bore 16 in the nose 18 of the body head portion and is of a length such that its loop 17 remote from the anchored end of the pull wire projects beyond such nose.

Twin abutment projections 19 projecting straight beyond the nose 18 of the body head portion have parallel surfaces 20 spaced apart a distance greater than the width of an orthodontic bracket 21 for forming a cavity so that the projections can straddle such bracket. The pull wire is of a length such that its free end loop 17, disposed in a plane perpendicular to the axis of pivot 4, will project beyond the thin rectangular tips 22 of the abutment projections 19 when the swing handle 3 is in its most forward position shown in FIG. 6. As shown in the drawings, particularly FIG. 2, the longer dimensions of such tips are approximately equal to the width of the cavity between parallel surfaces 20 of projections 19 and are parallel.

To pull from the face of a tooth T a bracket 21 bonded to it, the operator first hooks the free end loop 17 of the pull wire over a bracket ear or wing 23, as shown in FIGS. 6 and 7, or a similar projection. The operator then shifts the pistol nose 18 of the body head the position shown in FIG. 7 to the position shown in FIG. 8 so that the channel between the abutment projections 19 is substantially in registration with the bracket.

Next, the operator pulls the swing handle toward the pistol grip in the manner indicated in FIG. 9 to draw the tips 22 of the abutment projections 19 into bearing engagement with the face of the tooth T alongside opposite edges of the bracket 21, as shown best in FIG. 10. Further pulling of the swing handle toward the pistol grip to the position shown in FIG. 11 will draw the pull wire farther into the bore 16 so that its loop 17 engaged with the bracket wing will tilt the bracket relative to the tooth, as shown in FIGS. 11 and 12, and pull it free from the tooth. Because the load wire 12, the grip of the swing handle 3 and the fulcrum pivot 4 constitute a lever of the second class, the grip of handle 3 can be swung by applying light pressure to the grip through a considerable movement to exert a strong pull on the wire 12 and tooth bracket wing 23 with a very slight displacement, just enough to pull the bracket from the tooth, as shown by a comparison of FIGS. 9 and 11.

The bracket 21 is customarily bonded to a tooth face with epoxy resin, and such bond is ordinarily not strong enough so that the pull exerted on one corner wing by the puller, as described, will bend the base of the bracket as it is tilted to the position shown in FIGS. 11 and 12 from the position shown in FIGS. 9 and 10. In order to insure that the bracket will not be bent to constrict the arch wire slot 24, however, it is preferred that during the bracket-pulling operation such slot be filled by the spacer hook 25 of a spacer tenaculum 26 which fits snugly in the arch wire slot. As shown in FIG. 5, the puller can be held in one hand and the tenaculum can be held in the other hand with its tip fitted in the bracket arch wire slot. When the bracket is freed from the tooth after it is tilted to the position shown in FIGS. 11 and 12, the tenaculum will prevent the bracket from escaping from the loop 17 so that the bracket can be released and deposited in a controlled manner. Also, filling the orthodontic slot 24 with the spacer hook 25 of the tenaculum will prevent the base of the bracket from being bent by the pulling action so as to constrict the arch wire slot 24.

Application of the pulling force to a wing 23 of an orthodontic bracket 21 bonded to the face of a tooth T requires that there be an equal reaction force. If such reaction force is applied indirectly through the operator and the patient, the membrane between the root of the tooth and the jawbone will be pressed, causing the patient pain and perhaps trauma. If the reaction force is transmitted directly to the portion of the tooth face underlying the base of the bracket, such as would occur in a prying or wedging operation, such reaction normally is accompanied by working of the tooth relative to the jawbone which again presses the tooth root membrane, causing pain. The prying or wedging action may require a further reaction, such as by the application of force to the incisal edge of the tooth, the enamel of which is brittle, so that such tooth edge may be chipped or otherwise injured.

In the operation of pulling a bracket from a tooth face by the operation described above, the reaction to the pulling force is applied to the tooth to which the bracket is bonded, preferably being applied to the tooth face alongside the bracket by at least one, and preferably both, of the abutment projections 19. Such close coupling of the pulling force and the reaction force avoids the application of any appreciable pressure to the tooth root membrane and consequently avoids the pain which such pressure could cause.

The stroke of the pull wire effected by pulling the swing handle 3 from its extreme forward position to its rearmost position is adequate to enable the loop 17 to be hooked onto a bracket wing conveniently and to insure that the bracket will be freed from the tooth by pulling the swing handle to its limited retraction position, but because the swing handle lever is of the second-class type, the movement of the wire loop is much smaller than the movement of the swing handle. The shoulders 10 of the swing handle should engage the margins 11 of the body head portion cavity before the loop 17 draws the bracket into tight engagement with the puller nose channel cavity between the abutment projections 19.

While the pull wire loops 12 and 17 are shown as being separated by a twist so that that the planes of the respective loops are mutually perpendicular, the plane of the socket 13 could be turned 90 degrees and the pull wire could be formed of a single loop or of two coplanar loops which would be parallel to the inner faces 20 of the abutment projections 19 and perpendicular to the axis of the swing handle fulcrum pivot 4. In such case, the anchor screw for the pull wire will extend through the socket receiving the loop of the pull wire to be anchored at a direction parallel to the pivot 4 instead of perpendicular to it as shown in FIG. 3.

Alternatively, the pull wire could be a single loop or have coplanar loops with the free end loop 17 in a plane parallel to pivot 3 instead of being in a plane perpendicular to such pivot. In that case, it would be necessary for the thin rectangular tips 22 of the twin abutment projections 19 to project beyond the body head portion nose 18 in planes parallel to the axis of pivot 3, instead of in planes perpendicular to such axis as shown in FIG. 4, for example. With the twin abutment projections projecting in this attitude, it would, of course, be necessary to change the position in which the puller is held from that shown in FIG. 5. The operation of the puller would, however, be similar to that described above.

We claim:

1. A puller for pulling off a tooth an orthodontic bracket bonded to the tooth which bracket has at least one wing, comprising pulling means engageable with a wing of the orthodontic bracket, second-class force-applying lever means for exerting a pulling load force on said pulling means much greater than the power force applied to said lever means while said reaction means is simultaneously applied to the tooth including a lever arm having a fulcrum adjacent to one end, the opposite of said lever arm forming a handle, said pulling means being connected to said lever arm at a location at the same side of said fulcrum as said handle and spaced from said fulcrum a distance which is a small fraction of the length of said lever arm, and reaction means for applying reaction force from said fulcrum to the same tooth simultaneously with the application of pulling force to said pulling means by said force-applying lever means.

2. A puller for pulling off a tooth an orthodontic bracket bonded to the tooth which bracket has at least one wing, comprising pulling means engageable with a wing of the orthodontic bracket, reaction means for applying reaction force from said pulling means to the same tooth including abutment projection means having thin rectangular tips with their longer dimensions parallel and said tips engaging the tooth alongside the orthodontic bracket at locations spaced apart a distance approximately equal to the longer dimension of one of said tips, and second-class force-applying lever means for exerting a pulling load force on said pulling means much greater than the power force applied to said lever means while said reaction means is simultaneously applied to the tooth.

3. A puller for pulling off a tooth an orthodontic bracket bonded to the tooth which bracket has at least one wing, comprising pulling means engageable with a wing of the orthodontic bracket, reaction means for applying reaction force from said pulling means to the same tooth, and second-class force-applying lever means for exerting a pulling load force on said pulling means much greater than the power force applied to said lever means while said reaction means is simultaneously applied to the tooth, said pulling means including a double loop pull wire having a first loop hooked on the bracket wing and a second loop attached to the force-applying lever means.

4. The puller defined in claim 3, including a body having a cavity housing the second pull wire loop and having abutment projection means projecting from said body, engageable with the tooth and forming a channel embracing and shielding the first loop of the pull wire.

5. The puller defined in claim 4, in which the body cavity houses the portion of the lever means to which the second pull wire loop is attached.

6. The puller defined in claim 3, in which the body includes a pistol grip at the side of the lever means remote from the reaction means and located at one side of the pull wire, and the lever means includes a fulcrum pivot located at the opposite side of the pull wire.

7. The puller defined in claim 5, the body having a pistol grip, the lever arm extending from its fulcrum pivot generally parallel to said pistol grip and located between said pistol grip and the reaction means, and the pull wire projecting from the side of the lever arm remote from said pistol grip.

8. The puller defined in claim 4, in which the abutment projection means includes twin projections forming the channel and the body has a bore connecting the body cavity and the channel through which the pull wire extends.

9. A puller for pulling off a tooth an orthodontic bracket bonded to the tooth which bracket has at least one wing, comprising pulling means engageable with a wing of the orthodontic bracket, reaction means for applying reaction force from said pulling means to the same tooth, second-class force-applying lever means for exerting a pulling load force on said pulling means much greater than the power force applied to said lever means while said reaction means is simultaneously applied to the tooth, a body having a cavity, said lever means including a swing handle having an end portion received in said body cavity, a fulcrum pivot in said body cavity connecting said body and said end portion of said swing handle inserted in said body cavity, and the pulling means being connected to said swing handle end portion in said body cavity at a location spaced from said pivot.

10. A puller for pulling off a tooth an orthodontic bracket bonded to the tooth which bracket has at least one wing, comprising pulling means engageable with a wing of the orthodontic bracket, reaction means for applying reaction force from said pulling means to the same tooth, second-class force-applying lever means for exerting a pulling load force on said pulling means much greater than the power force applied to said lever means while said reaction means is simultaneously applied to the tooth, a body carrying said reaction means and having a cavity, a swing handle connected to said pulling means and having an end portion projecting into said body cavity and pivoted to said body and its other end portion being located exteriorly of said body cavity and spaced from said reaction means, and spring means lodged in said body cavity and engaged between said swing handle end portion projecting into said body cavity and said body for urging said swing handle toward said reaction means.

11. The puller defined in claim 10, in which the spring means includes a strip spring having one end portion anchored to the end portion of the swing handle projecting into the body cavity and its other end portion bearing against the wall of the body cavity.

12. A puller for pulling off a tooth an orthodontic bracket bonded to the tooth, which bracket has at least one wing, comprising a lever arm having fulcrum pivot means adjacent to one end and a force-receiving opposite end handle portion disposed in spaced relationship by a lever arm intermediate portion located between said fulcrum pivot means and said handle portion, a body carrying said fulcrum pivot means, a substantially straight pull wire engageable with a wing of the orthodontic bracket having its length extending transversely of said lever arm and connected to said lever arm intermediate portion at a location between said fulcrum pivot means and said force-receiving opposite end handle portion of said lever arm, and reaction means carried by said body for transmitting reaction force from said fulcrum pivot means to the tooth to which the bracket is bonded.

13. A puller for pulling off a tooth an orthodontic bracket bonded to the tooth which bracket has at least one wing, comprising a substantially straight pull wire having a loop on one end engageable with a wing of the orthodontic bracket, a body having a cavity and a bore leading therefrom housing a portion of said pull wire, force-applying means connected to the other end of said pull wire within said body cavity for drawing said pull wire farther into said body bore and cavity, and reaction projections projecting from said body beyond said body bore alongside opposite sides of said pull wire and engageable with the tooth to which the bracket is bonded for applying reaction force from said body to such tooth.

14. A puller for pulling off a tooth an orthodontic bracket bonded to the tooth which bracket has at least one wing, comprising pulling means engageable with a wing of the orthodontic bracket, a body having a cavity housing a portion of said pulling means, force-applying means connected to said pulling means for drawing said pulling means farther into said cavity, and reaction means for applying reaction force from said body to the tooth to which the bracket is bonded, said force-applying means including lever means having fulcrum pivot means in said body cavity.

15. A method of removing an orthodontic bracket bonded to a tooth face and having a projecting wing which comprises applying a pulling force to such orthodontic bracket wing and simultaneously transmitting reaction force to the same tooth.

16. A method of removing an orthodontic bracket bonded to a tooth face and having a projecting wing which comprises applying a pulling force to such orthodontic bracket wing and thereby pulling the bracket off the tooth face and simultaneously transmitting reaction force to the tooth face alongside the bracket.

17. The method defined in claim 16, including transmitting the reaction force to two locations on the tooth face at opposite sides of the bracket.

18. The method defined in claim 15, in which the pulling force tilts the bracket relative to the tooth face in pulling the bracket from the tooth face.

19. The method defined in claim 18, in which the bracket has an arch wire groove and the method includes filling such arch wire groove during application of the pulling force to the orthodontic bracket wing to prevent the groove being constricted by tilting of the bracket.

20. The method defined in claim 15, including hooking a wire loop around the orthodontic bracket wing and exerting a pulling force on such wire loop.

21. The method defined in claim 16, including pressing an abutment against the tooth face alongside the bracket for transmitting reaction force to the tooth face.

* * * * *

UNITED STATES PATENT AND TRADEMARK OFFICE
CERTIFICATE OF CORRECTION

PATENT NO. : 4,553,932

DATED : November 19, 1985

INVENTOR(S) : Armstrong et al.

It is certified that error appears in the above-identified patent and that said Letters Patent are hereby corrected as shown below:

Column 6, line 9:   Cancel "5" and insert ...12...

Signed and Sealed this

Twenty-ninth Day of April 1986

[SEAL]

Attest:

DONALD J. QUIGG

Attesting Officer

Commissioner of Patents and Trademarks